US00PP19654P2

(12) United States Plant Patent
Swanson et al.

(10) Patent No.: US PP19,654 P2
(45) Date of Patent: Jan. 20, 2009

(54) ***CERCIS* TREE NAMED 'GRESWAN'**

(50) Latin Name: *Cercis canadensis*
Varietal Denomination: Greswan

(75) Inventors: Kerry Swanson, Park Hill, OK (US); Danny Fountain, Park Hill, OK (US)

(73) Assignee: Greenleaf Nursery Company, Park Hill, OK (US)

( * ) Notice: Subject to any disclaimer, the term of this patent is extended or adjusted under 35 U.S.C. 154(b) by 0 days.

(21) Appl. No.: 11/894,974

(22) Filed: Aug. 22, 2007

(51) Int. Cl.
*A01H 5/00* (2006.01)

(52) U.S. Cl. ..... Plt./216

(58) Field of Classification Search ..... Plt./216
See application file for complete search history.

(56) References Cited

U.S. PATENT DOCUMENTS

PP18,528 P2 * 2/2008 Bennett ..... Plt./216

* cited by examiner

*Primary Examiner*—Wendy C. Haas
(74) *Attorney, Agent, or Firm*—Penny J. Aguirre

(57) ABSTRACT

A new cultivar of *Cercis Canadensis* named 'Greswan', characterized by its continuous production of burgundy colored new foliage (both upper and lower surface) throughout the growing season, its multicolored effect when combined with mature green foliage, its burgundy stems and petioles, its distinctively heart-shaped leaves, its purple pink flowers emerging in early spring, its hardiness to U.S.D.A Zone 5, and its ease of propagation by budding.

2 Drawing Sheets

Botanical classification: *Cercis canadensis.*
Variety denomination: 'Greswan'.

BACKGROUND OF THE INVENTION

The present invention relates to a new and distinct cultivar of *Cercis canadensis,* and will be referred to hereafter by its cultivar name, 'Greswan'. 'Greswan' is an Eastern redbud tree grown for use as a landscape plant.

The new *Cercis* was discovered by the inventors in spring of 2000 in Park Hill, Okla. as a naturally whole plant mutation derived from seed sown from unnamed plants of *Cercis canadensis* after evaluation of approximately 3,000 seedlings.

Asexual reproduction of the new cultivar was first accomplished by budding onto rootstock in August 2003 in Fort Gibson, Okla. The characteristics of this cultivar have been determined to be stable and are reproduced true to type in successive generations.

SUMMARY OF THE INVENTION

The following traits have been repeatedly observed and represent the characteristics of the new cultivar as observed for six years in Park Hill, Okla. These attributes in combination distinguish 'Greswan' as a unique cultivar of *Cercis canadensis.*

1. 'Greswan' exhibits glossy new foliage that is burgundy in color and gradually matures to a dark green color. 'Greswan' produces new foliage through the growing season that is burgundy in color. The combination of the green foliage of the mature leaves and the burgundy color of the new leaves produces a multicolored effect.
2. The leaves of 'Greswan' are burgundy in color on both the upper and lower leaf surfaces.
3. The petioles and stems of new growth of 'Greswan' are burgundy in color.

4. 'Greswan' has distinctively heart-shaped leaves.
5. 'Greswan' blooms in early spring with purple-pink colored flowers emerging from deep purple-pink colored flower buds.

'Greswan' is unique in comparison to the parent species, *Cercis canadensis,* in having burgundy colored foliage rather than green. The closest comparison plant is *Cercis canadensis* 'Forest Pansy'. 'Forest Pansy' (not patented) is the closest comparison plant and is similar to the new *Cercis* in having burgundy foliage. 'Greswan' differs from 'Forest Pansy' in producing new foliage that is burgundy in color the entire growing season whereas the foliage of 'Forest Pansy' turns green in late spring to early summer in the southern region of the U.S and in mid summer in the northwestern region of the U.S. In addition, the lower leaf surface of 'Greswan' is burgundy whereas the lower leaf surface of 'Forest Pansy' is green, the mature foliage of 'Greswan' is darker green in color and the leaf shape of 'Greswan' is more distinctly heart shaped.

BRIEF DESCRIPTION OF THE DRAWING

The accompanying colored photographs of 'Greswan' illustrate the overall appearance and distinct characteristics of the new *Cercis* as grown in Park Hill, Okla.

Figure 1:
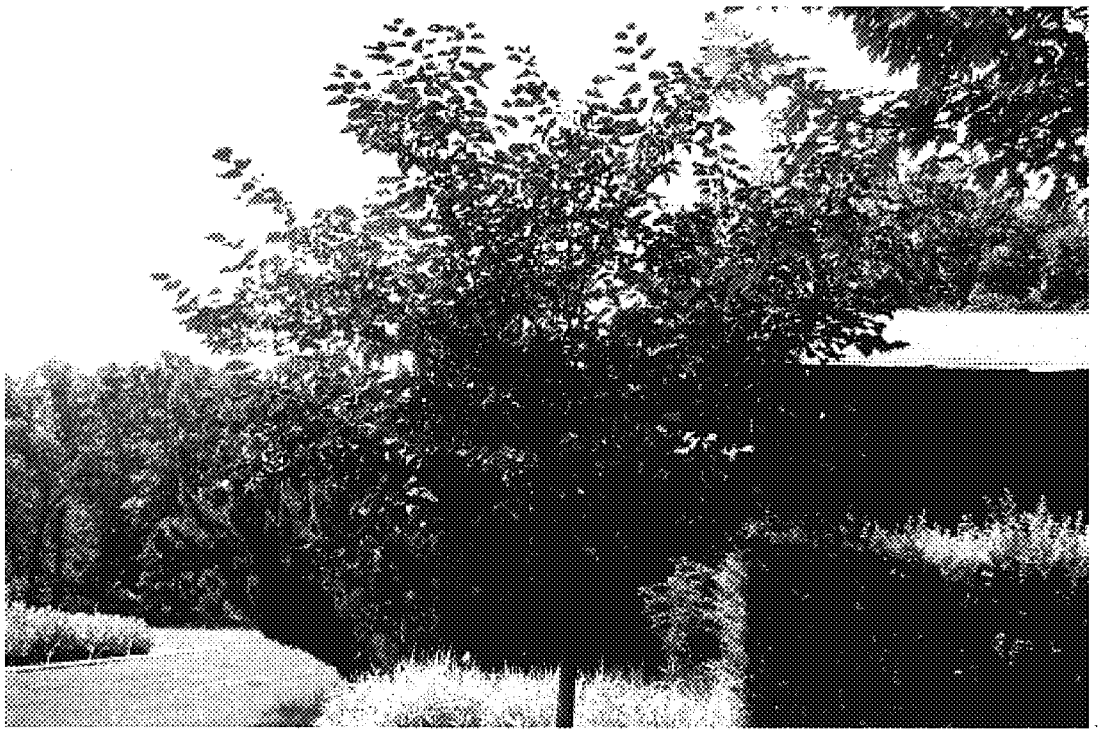
FIG. 1 is a view of a seven year-old plant of 'Greswan' and provides a view of the plant habit and multicolored foliage effect, FIG. 2 provides a close-up view of the upper surface of leaves of 'Greswan' and FIG. 3 provides a close-up view of the lower surface of leaves of 'Greswan'.
Figure 2:
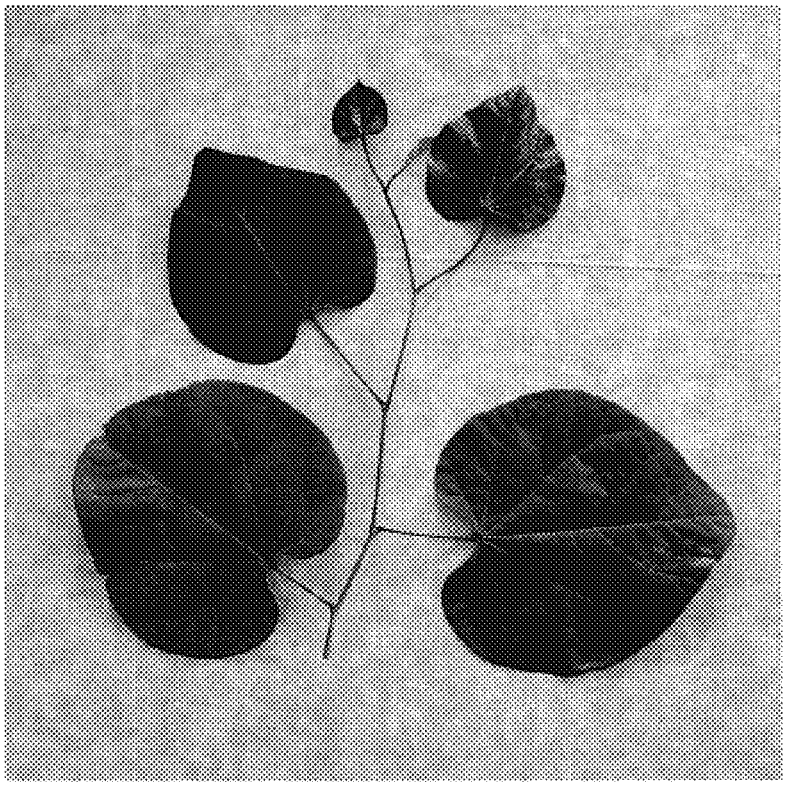
Figure 3:
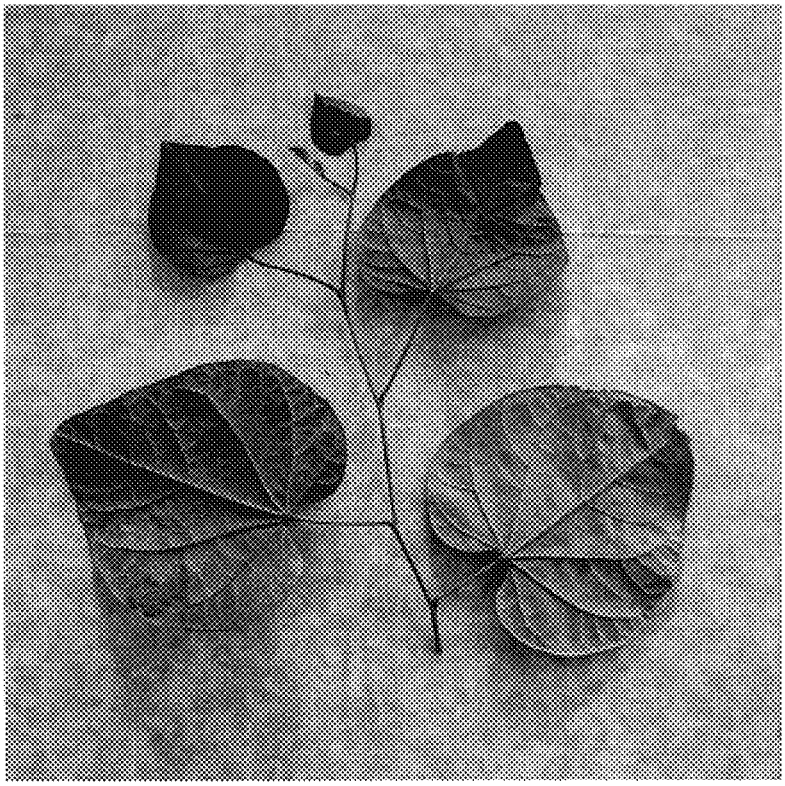

The colors in the photographs are as close as possible with the digital photography techniques available, the color values cited in the detailed botanical description accurately describe the colors of the new *Cercis.*

DETAILED BOTANICAL DESCRIPTION

The following is a detailed description of a 4 year-old plant of the new cultivar as grown outdoors and finished in a 5-gallon container in Park Hill, Okla. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Greswan' is a cultivar of *Cercis canadensis.*

*Parentage.*—Naturally occurring whole plant mutation of *Cercis canadensis.*

*Plant habit.*—Deciduous tree with an spreading habit with horizontally tiered branches.

*Height and spread.*—Reaches about 6 to 7.6 m (20 to 25 ft) in height and spread in seven years of growth in Oklahoma.

*Cold hardiness.*—U.S.D.A. Zones 5.

*Diseases and pests.*—No susceptibility or resistance to diseases or pests has been observed.

*Root description.*—Fibrous, freely branched.

Growth and propagation:

*Propagation.*—Budding; typically grown for one year as a root stock in the field, budded in the fall of the first year, the bud is forced for one year in the field and then planted in a 5-gallon container.

*Growth rate.*—Moderately vigorous.

Stem description:

*Shape.*—Round to slightly oval, slightly zig-zag in growth habit.

*Stem color.*—Branches (when in bud); 200A with numerous small lenticels 159C and a overlay of N200D, young branches; N77A, bark; base of N186C with heavy coverage of lenticels 159C and and suffused with 159C.

*Stem diameter* (*4 year-old tree*).—Main trunk; average of 3 cm, branches; average of 8 mm, young stems; average of 3 mm.

*Stem surface.*—Smooth, and satiny on young twigs, bark is relatively smooth with abundant lenticels.

*Internode length.*—About 1.5 to 5 cm (average 3.5 cm).

Foliage description:

*Leaf shape.*—Cordate.

*Leaf division.*—Simple.

*Leaf base.*—Cordate.

*Leaf apex.*—Acute.

*Leaf fragrance.*—None.

*Leaf venation* (*upper and lower surface*).—Palmate, most prominent on base region and on young leaves, 146B in color on young leaves (upper and lower surface), 146C suffused with 187B on mature leaves.

*Leaf margins.*—Entire.

*Leaf arrangement.*—Alternate.

*Leaf aspect.*—Held slightly downward from petiole (hanging) and can be slightly reflexed.

*Leaf attachment.*—Petiolate.

*Leaf surface* (*upper and lower leaves*).—Smooth with satin sheen on newly formed leaves, becoming very glossy when fully open, and glabrous when mature.

*Leaf size.*—Mature to about 10 cm in length and width.

*Leaf color.*—Newly expanding: upper and lower surface; 137B with blush of N77, fully expanded upper surface; between N77A and 183A, fully expanded lower surface; 187A to 146A heavily mottled with 187A, mature foliage upper surface; color between 137A and 146A with varying degrees of blushing of 187A, mature foliage lower surface; closest to 137A with varying degrees of blushing of 187A.

*Petiole.*—Average of 5 cm in length and 2 mm in width, typically held horizontal to about 15° angle downward from branch, color N77A, surface glabrous and satiny.

Inflorescence description:

*Inflorescence type.*—Cauliflorous clusters of papilionaceous (pea-like) flowers.

*Inflorescence size.*—Up to 5.5 cm in width and 3.5 cm in depth.

*Lastingness of inflorescence.*—2 to 3 weeks.

*Flower size.*—About 1.5 cm in depth and about 1.3 cm in diameter.

*Flower fragrance.*—Faint.

*Flower number.*—Average of 8 per node, 3 to 5 per inflorescence.

*Bracts.*—About 5 per inflorescence, imbricate, ciliate margins, translucent, 3 mm in length and 1 mm in width, 137C with 177A near apex.

*Peduncle.*—Stout, 2 mm long, 1 mm wide, 137B in color, pubescent.

*Pedicel.*—About 1.8 cm in length, about 1 mm in width, 79A in color, glabrous surface.

*Flower buds.*—Cone-shaped, about 5 mm in length and 2 mm in width, 59A to 59B with a base of N79A, calyx portion same as open flowers.

*Flower type.*—Papilionaceous.

*Calyx.*—Broad Campanulate in shape, about 4 mm in depth and 5 mm in diameter, glabrous surface, 71A in color with a base of 59A, comprised of 5 fused sepals.

*Corolla features.*—Papilionaceous-like (5 segments); a two outer petals, a center petal and an inner lip; comprised of two lobes that are folded around stamens and pistil, outer and center petals; oblong in shape, about 1 cm in length and 4 mm in width, base cuneate to a short colorless claw, color N80D to N80C with center petal also mottled with N80B, inner lip; ovate in shape, about 1.1 cm in length and 5 mm in width, base cuneate to a short colorless claw, color N80B, all segments; glabrous in texture, entire margin, rounded apex.

*Receptacle.*—Disk-shaped, gelatinous, 144B in color, about 2 mm in diameter and 1 mm in depth.

Reproductive organs:

*Gynoecium.*—1 Pistil, about 1 cm in length, <1 mm in width; style is 71C in color; stigma about 0.3 mm in diameter, 145C in color; ovary is superior 137B in color, 3.5 mm in length and 1 mm in width with a stipe 1 mm in length.

*Androcoecium.*—About 10 stamens, not united, 1.1 cm in length and 1 mm in width; filament is 1 cm in length, <1 mm in width and 69C in color; anther is basifixed, 1 mm in length, 0.5 mm in width and 200B in color, pollen is abundant and 161A in color.

*Fruit.*—None observed on the plant used for data collection.

We claim:

1. A new and distinct cultivar of *Cercis canadensis* plant named 'Greswan' as herein illustrated and described.

* * * * *